United States Patent [19]
Gambale et al.

[11] Patent Number: 6,074,339
[45] Date of Patent: Jun. 13, 2000

[54] EXPANDABLE BRAID DEVICE AND METHOD FOR RADIATION TREATMENT

[75] Inventors: Richard A. Gambale, Tyngsboro; James William Moriarty, Jr., Westford, both of Mass.; Cheryl Milone Bab, New York, N.Y.

[73] Assignee: Medtronic AVE, Inc., Santa Rosa, Calif.

[21] Appl. No.: 09/073,993

[22] Filed: May 7, 1998

[51] Int. Cl.$^7$ .................................................. A61M 5/00
[52] U.S. Cl. ................................................................ 600/3
[58] Field of Search ............................ 600/1–8; 606/191, 606/194, 195; 604/96–101

[56] References Cited

U.S. PATENT DOCUMENTS

| | | |
|---|---|---|
| 4,763,671 | 8/1988 | Goffinet . |
| 4,819,618 | 4/1989 | Liprie . |
| 5,199,939 | 4/1993 | Dake et al. . |
| 5,213,561 | 5/1993 | Weinstein et al. . |
| 5,282,781 | 2/1994 | Liprie . |
| 5,302,168 | 4/1994 | Hess . |
| 5,354,257 | 10/1994 | Roubin et al. . |
| 5,411,466 | 5/1995 | Hess . |
| 5,484,384 | 1/1996 | Fearnot . |
| 5,498,227 | 3/1996 | Mawad . |
| 5,549,581 | 8/1996 | Lurie et al. . |
| 5,573,509 | 11/1996 | Thornton . |
| 5,618,266 | 4/1997 | Liprie . |
| 5,643,171 | 7/1997 | Bradshaw et al. . |
| 5,653,684 | 8/1997 | Laptewicz et al. ..................... 604/22 |
| 5,683,345 | 11/1997 | Waksman et al. . |
| 5,728,042 | 3/1998 | Schwager ................................ 600/3 |
| 5,730,698 | 3/1998 | Fischell et al. ........................ 600/3 |
| 5,863,285 | 1/1999 | Coletti .................................... 600/3 |

FOREIGN PATENT DOCUMENTS

| | | |
|---|---|---|
| 1 197 631 | 12/1985 | Canada . |
| 0 152 124 | 8/1985 | European Pat. Off. . |
| 0 433 011 A1 | 6/1991 | European Pat. Off. . |
| 0 497 495 A2 | 8/1992 | European Pat. Off. . |
| 0 497 495 A3 | 8/1992 | European Pat. Off. . |
| 0 593 136 A1 | 4/1994 | European Pat. Off. . |
| 0 688 580 A1 | 12/1995 | European Pat. Off. . |
| 0 826 393 | 3/1998 | European Pat. Off. . |
| 793158 | 4/1958 | United Kingdom . |
| 1219604 | 1/1971 | United Kingdom . |
| 1558127 | 12/1979 | United Kingdom . |
| WO 85/02779 | 7/1985 | WIPO . |
| WO 90/03827 | 4/1990 | WIPO . |
| WO 93/04735 | 3/1993 | WIPO . |

OTHER PUBLICATIONS

"Restenosis After PTCA Prevented By Radiation Therapy" by Individual, Inc., *The Financial Times*, Mar. 4, (1997).

"Low–Dose, β–Particle Emission From [Stent] Wire Results in Complete, Localized Inhibition of Smooth Muscle Cell Proliferation" by Tim A. Fischell, M.D. et al., *Circulation*, vol. 90, No. 6, Dec., 1994, pp. 2956–2962.

"Low–Dose, Radioactive Endovascular Stents Prevent Smooth Muscle Cell Proliferation and Neointimal Hyperplasia in Rabbits" by Christoph Hehrlein, M.D. et al., *Circulation*, vol. 92, No. 6, Sep. 15, 1995, pp. 1570–1575.

"Inhibition of Neointimal Proliferation With Low–Dose Irradiation From a β–Particle–Emitting Stent" by John R. Laird, M.D. et al., *Circulation* vol. 93, No. 3, Feb. 1, 1996, pps. 529–536.

Catheter–Based Radiotherapy to Inhibit Restenosis After Coronary Stenting, The New England Journal of Medicine, vol. 336, No. 24, pp. 1697–1703, Jun. 12, 1997.

*Primary Examiner*—Samuel G. Gilbert
*Attorney, Agent, or Firm*—Sterne Kessler Goldstein & Fox P.L.L.C.

[57] ABSTRACT

An expandable braid device attached to a guidewire acts to both house radiation and to expose a stenosis site to such radiation as a function of the braid's collapsed or deployed configuration. The expandable braid device, in a closed configuration, shields a radioactive inner core of the braid as it is advanced to and located at a stenosis site and, in an expanded configuration, exposes the radioactive inner core to the stenosis site in order to irradiate such site.

28 Claims, 4 Drawing Sheets

EXPANDABLE BRAID DEVICE AND METHOD FOR RADIATION TREATMENT

FIELD OF THE INVENTION

This invention generally relates to radiation therapy for preventing restenosis. More particularly, this invention relates to a device and a method for irradiating a stenosed region of an artery by use of a radiation source.

BACKGROUND OF THE INVENTION

The treatment of a stenosis site to prevent restenosis after angioplasty using radiation is well known. Angioplasty (also referred to as percutaneous transluminal angioplasty (PTA)) is a non-surgical technique for unblocking vascular lumens resulting from peripheral and coronary vascular disease. This technique has become an accepted form of treatment both in the United States and internationally. Another form of treating vascular disease is atherectomy, a surgical procedure for the same purpose of removing stenotic lesions from arteries.

In typical angioplasty procedures, a guiding catheter is percutaneously introduced into the vascular system of a patient's body through an artery. Once inserted, the guiding catheter is maneuvered through the vascular artery until the distal tip of the guiding catheter is positioned proximal to the lesion site. A guide wire and a balloon catheter are then introduced through the guiding catheter. First, the guide wire is advanced through the distal tip of the guiding catheter until the distal end of the guide wire moves past the lesion to be dilated. Then, the balloon catheter is advanced over the guide wire to a location such that the balloon on the distal end portion of the catheter is positioned inside the atherosclerotic narrowing of the artery. The angioplasty procedure may then begin by inflating the balloon to a predetermined size, thereby compressing the atheroma. This enlarges the atherosclerotic narrowing and enlarges the lumen by stretching the vessel wall. After a predetermined period of time, the balloon is deflated and removed.

However, a recurrent problem following angioplasty is that excessive tissue growth may occur at the site of the balloon catheter, thereby causing the development of further blockage or renarrowing of the diseased vessel; this can also occur after an atherectomy procedure. This problem, called restenosis, is thought to be part of a natural healing process after stretching the vascular structure during angioplasty. It is caused by fibrointimal proliferation of the stretched wall in which the cells lining the vascular interior multiply and form fibrous tissue. Restenosis can result in the necessity of repeating the angioplasty or atherectomy procedure.

The successful use of radiation therapy to prevent the growth of such fibrous tissue after an angioplastic or an atherectomy procedure, thereby reducing the tendency for restenosis, is well known. In general, such radiation therapy consists of exposing the stenosis or treatment site to radiation. The effective dose to inhibit restenosis depends on the type of radiation, e.g., Gamma or Beta radiation, as well as the devices and techniques used to deliver such radiation. In addition, the intensity of radiation source on the treatment site drops rapidly as a function of the distance of the radiation source to such treatment site. Accordingly, if the source is not held reasonably near the treatment site of the vascular pathway, the treatment site will receive less than the prescribed dosage of radiation. Under dosing the treatment site will reduce the effectiveness of radiation therapy such that restenosis is not prevented or is even exacerbated. Similarly, the portion of the pathway which is not stenosed but is nearest the radiation source will receive an excess dose of radiation. Application of radiation to a healthy portion of the vessel wall is harmful. For example, overdosing of a section of blood vessel can cause arterial necrosis, inflammation and hemorrhaging. In addition, improper exposure of healthy tissue to radiation may occur not only during the treatment period but also during delivery of the radiation to the treatment site. As a result, while radiation therapy has been found to prevent restenosis, its use must be carefully controlled to maximize exposure to the treatment site while minimizing exposure to healthy portions of the vascular pathway.

The following United States Letters Patents disclose various embodiments for radiation therapy: U.S. Pat. No. 5,643,171 to Bradshaw et al.; U.S. Pat. No. 5,498,227 to Mawad; U.S. Pat. No. 5,484,384 to Fearnot; U.S. Pat. No. 5,411,466 to Hess; U.S. Pat. No. 5,302,168 to Hess and U.S. Pat. No. 5,213,561 to Weinstein et al. These patents are incorporated in their entireties herein by reference. The devices and methods described in the foregoing patents in general expose a stenosis site to radiation using two general approaches. For the first general approach, a catheter includes a structure at its distal end which functions to expose the treatment site to radiation (hereinafter referred to as an exposure structure). Examples of such exposure structures are ventilation features (such as apertures or slits) in the catheter or in a balloon attached to such catheter, or a helical spring, expandable cage or other wire structure. In addition, the catheter contains a treatment channel used for delivering the radiation source to the catheter's distal end. Using this approach, the distal end of the catheter can be precisely positioned at the treatment site before delivering the radiation source. Thereafter, the radiation source can be delivered for precise placement at the treatment site such that it maximizes irradiation of the treatment site while minimizing irradiation of healthy tissue in the vascular pathway.

For the second general approach, the exposure structure at the distal end of the catheter (or other carrier device to which the exposure structure can be attached, such as, for example, a guidewire) can have the radiation source attached to it before insertion into the vascular pathway. However, using this approach, the radiation source exposes the healthy tissue of the pathway along the path traversed to deliver such radiation source to the treatment site. Therefore, some known devices and methods have the disadvantage of exposing healthy tissue to radiation as a by-product of irradiating the treatment site.

However, for other known devices and methods of the second general approach, a provision is made for shielding the radiation source in the distal end of the carrier device prior to initiation of irradiation procedure. For example, the exposure structure on which the radiation source is attached is contained within a structure separate from the exposure structure (hereinafter referred to as a shielding structure). The shielding structure in turn does not have any apertures or other ventilation features through which the radiation source can expose the vascular pathway outside such shielding structure. In effect, the exposure structure is housed prior to initiating the irradiation treatment. Then, either the exposure or shielding structure is moved or otherwise manipulated to free the exposure structure from the shielding structure such that the radiation source is exposed to the stenosis site. However, these known devices and methods have the disadvantage of integrating an exposure structure with a shielding structure for use in the procedure. As a result, for example, the combined structures are more rigid.

This impacts the physician's ability to track the carrier device through the tortuous arteries because greater rigidity makes maneuvering the carrier device more difficult, resulting in a more complicated procedure. In addition, with two structures, malfunctions of either structure render the irradiation procedure unsuccessful. Thereby, the chance of a successful procedure is decreased.

In addition, where any of the above malfunctions or complications occurs, the period of time that the radiation source is present in the patient's body as well as the length of time required to successfully complete the irradiation procedure will be increased. This results in increasing the patient's exposure to medical risks inherent in the irradiation procedure as well as more general medical procedure risks. The likelihood of additional complications for the patient is thereby also increased.

Accordingly, there is a need to improve the heretofore known devices and methods, in order to overcome the above described shortcomings in the known devices and methods.

SUMMARY OF THE INVENTION

The present invention is directed to, in one embodiment, an expandable braid device attached to a wire which acts to both house radiation and to expose a stenosis site to such radiation as a function of the braid's collapsed or deployed configuration. The expandable braid device, in a closed configuration, shields a radioactive inner core of the braid as it is advanced to and located at a stenosis site and, in an expanded configuration, exposes the radioactive inner core to the stenosis site in order to irradiate such site.

The present invention overcomes the shortcomings of known devices and techniques by simplifying the device used to irradiate the stenosis site. More particularly, the wire (or other carrier) includes a single structure, an expandable braid, which operates to both shield and expose the radiation source attached to the expandable braid's inner core. The wire containing such single structure is simplified and less rigid than one containing integrated structures. Therefore, malfunctions and complications are reduced such that the likelihood of a successful irradiation procedure is increased.

We have also found that with the present invention, the expandable braid provides a combination of functions in a single structure. In addition to the functions of shielding and exposing radiation, upon deployment, the radiation treatment applied to the stenosis site is radially uniform based on centering the radiation source within the braid. Accordingly, the braid also exposes the radiation equidistant from the vascular walls so that the radiation source is centered in the lumen of the vascular pathway. Furthermore, the braid provides the following additional functions: when deployed, it can exert a radial force against the artery for application of pressure (where necessary) to the vessel wall and for securing the placement of the radiation source during radiation treatment; it allows blood to flow distally during the irradiation procedure; and it optimizes safety in delivering, exposing and removing the radiation source by preventing it from breaking free of the wire should it become detached from the braid's inner core.

In addition, an alternative embodiment of the present invention also provides variations in the amount of radiation applied to the stenosis site based on the mechanism which operates the braid supporting partial rather than complete deployment of the braid. With partial deployment, the expandable braid attenuates more radiation then where the braid is completely deployed but less than where the braid is collapsed. In addition, this relationship applies to a wide range of partial deployment configurations. In this way, the physician can vary the amount of radiation to which the stenosis site is exposed by controlling the level of deployment of the expandable braid rather than having to replace the expandable braid device with another device containing a different quantity of radiation. This increases the flexibility of providing irradiation treatments within a range of dosages using the single structure, namely, the expandable braid containing the radiation source.

Moreover, in additional alternative embodiments of the present invention, an expandable spiral device can be used. Also, in addition to the inner core, the radiation source can be applied to the inner surface of the braid or spiral. As a result, the braid or spiral can supply dual radiation sources which are both shielded in the interior of the braid or spiral.

These and other features and advantages of the invention will be readily apparent from the following detailed description of certain embodiments taken in conjunction with the accompanying unscaled drawings.

DETAILED DESCRIPTION OF ILLUSTRATIVE EXEMPLARY EMBODIMENTS

Figure 1:
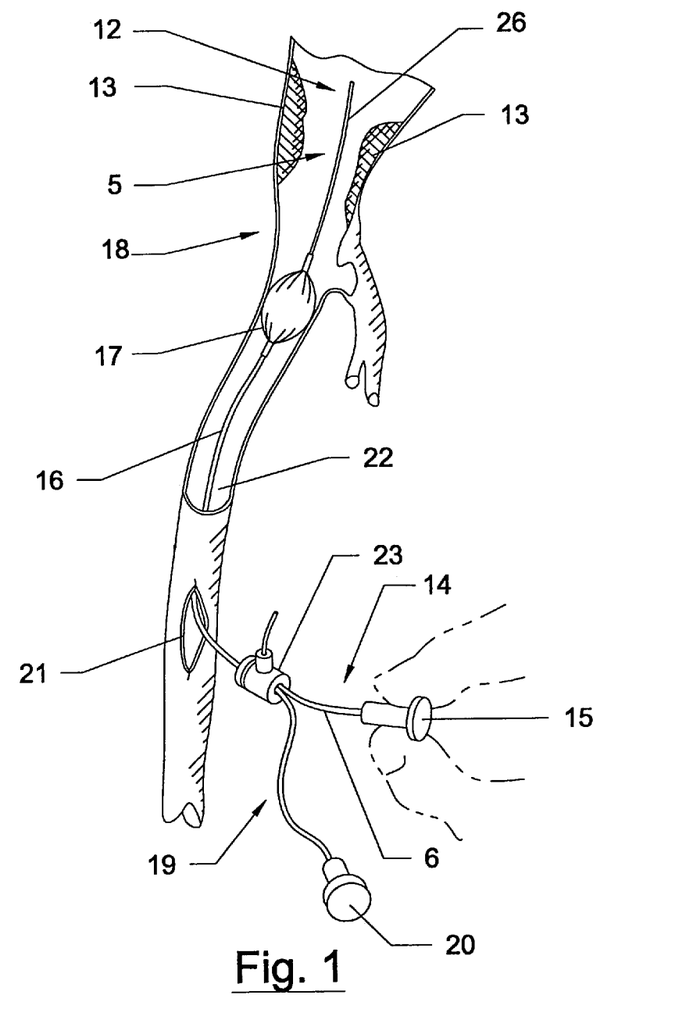
FIG. 1 is a perspective view of an expandable braid device constructed on a wire and positioned in a vascular pathway according to an illustrative embodiment of the present invention.

By way of overview and introduction, FIG. 1 is a perspective view of an expandable braid device 5 constructed according to an embodiment of the present invention. The device 5 includes an expandable braid 26 and is constructed as part of a wire 6. The wire 6 includes a distal end portion 12 and a proximal end portion 14. The device 5, in the illustrated embodiment, is located in the distal end portion 12. The placement of the device 5 at a stenosis site 13 as shown in FIG. 1, is achieved by manipulation of a proximal end portion 14 of the wire 6. In addition, the proximal end portion 14 includes a control mechanism 15 (for example, a knob) for controlling the deployment and collapse of the braid 26.

FIG. 1 also shows that the expandable braid device 5 on the wire 6 is exposed distally beyond a balloon catheter 16 (hereinafter referred to as the catheter). The catheter 16 generally includes a balloon 17 located at its distal end portion 18 for use in performing an angioplasty procedure. Placement of the balloon 17 (shown inflated for illustrative purposes only) is achieved by manipulation of a proximal end portion 19 of the catheter 16. In addition, the proximal end portion 19 includes a pressure control mechanism 20 (for example, an inflation device) for controlling the deployment and collapse of the balloon 17. As further shown in FIG. 1, the proximal ends 14 and 19 and their respective control mechanisms 15 and 20 can be operated by a physician to perform the angioplasty and irradiation procedures.

Further description of the expandable braid device 5 will be aided by describing the manner of use of such device 5. With general reference to FIG. 1, the stenosed region 13 of an artery is identified using an appropriate diagnostic procedure. Such procedures are well known in the art and are not described further herein. In the event that angioplasty is indicated, the physician makes a small incision 21 in the body to gain access to a vascular pathway 22. An introducer 23, including a short tapered tube with a proximal luer fitting (not shown), is then placed into the incision 21 to act as an initial guiding device and entry point for additional devices, such as the guide catheter (not shown), wire 6 and the catheter 16, placed into the pathway 22.

A guidewire (not shown) is then maneuvered into and advanced through the vascular pathway to a location past the stenosis site 13. This guidewire is separate from the wire 6 and is used as a support for maneuvering other devices through the pathway 22. Then, the catheter 16 (including the balloon 17, which is deflated) is inserted into the luer fitting, threaded over the guidewire and advanced so that the balloon 17 is positioned precisely at the stenosis site 13. The catheter 16 is imaged using fluoroscopy while being advanced through the pathway 22. In this way, the physician has a visual means of tracking the precise location of such devices. The physician uses the proximal end portion 19 of the catheter 16 to position the deflated balloon 17 at the precise location (the balloon 17 shown in FIG. 1 is proximal of the stenosis site 13). Once the catheter 16 is verified to be in position using fluoroscopy imaging, the balloon 17 can be inflated to start the angioplasty procedure. The balloon 17 remains in that position and is inflated and deflated one or more times to widen the constricted area.

At the appropriate time for the irradiation procedure, the catheter 16 is repositioned so that the balloon 17 is no longer at the stenosis site 13 (as shown in FIG. 1) and the guidewire on which the catheter 16 was threaded can be removed. In alternative embodiments, the guidewire on which the catheter 16 was threaded can remain in place. Either before or after relocating the catheter 16 so that the balloon 17 is no longer located at the stenosis site 13, the wire 6 is inserted into the catheter 16 through the luer fitting. The wire 6 is then threaded through the lumen of the catheter 16 and past the distal end portion 18 of the catheter 16 until the expandable braid device 5 is positioned precisely at the stenosis site 13. The resulting placement of the balloons 17 proximal to the stenosis site 13 and of the expandable braid device 5 at the stenosis site 13 is shown in FIG. 1. The physician again uses the proximal end portion 14 of the wire 6 to position the device 5 at the precise location (as shown in FIG. 1). With the expandable braid device 5 in place, the control mechanism 15 is operated by the physician to deploy the device 5. The device 5 acts as a housing for a radiation source 24 (shown in FIG. 3) located at an inner core 25 (shown in FIG. 3) of the wire 6. Such inner core 25 forms the radial center of the braid 26 in collapsed form. Moreover, when the braid 26 is collapsed, it acts as a surface over the radiation source 24 in order to shield the source 24. In this way, upon deployment of the expandable braid device 5, the radiation source 24 is exposed to the stenosis site 13 for the irradiation treatment. When the braid 26 is collapsed, the expandable braid device 5 shields the radiation source 24 from exposing the stenosis site 13 or healthy tissue within the vascular pathway 22.

Upon completion of the specified time period for irradiating the stenosis site 13, the control mechanism 15 is operated again in order to collapse the expandable braid device 5. The radiation source 24 can then be removed from the vascular pathway by withdrawing the wire 6 (and along with it, the expandable braid device 5).

Figure 2:
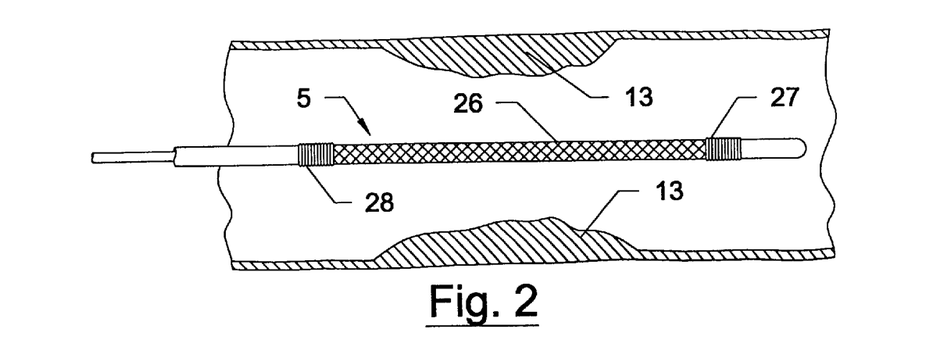
FIG. 2 is an enlarged longitudinal sectional view of the expandable braid device of FIG. 1 in a closed configuration and positioned at a stenosis site.
Figure 3:
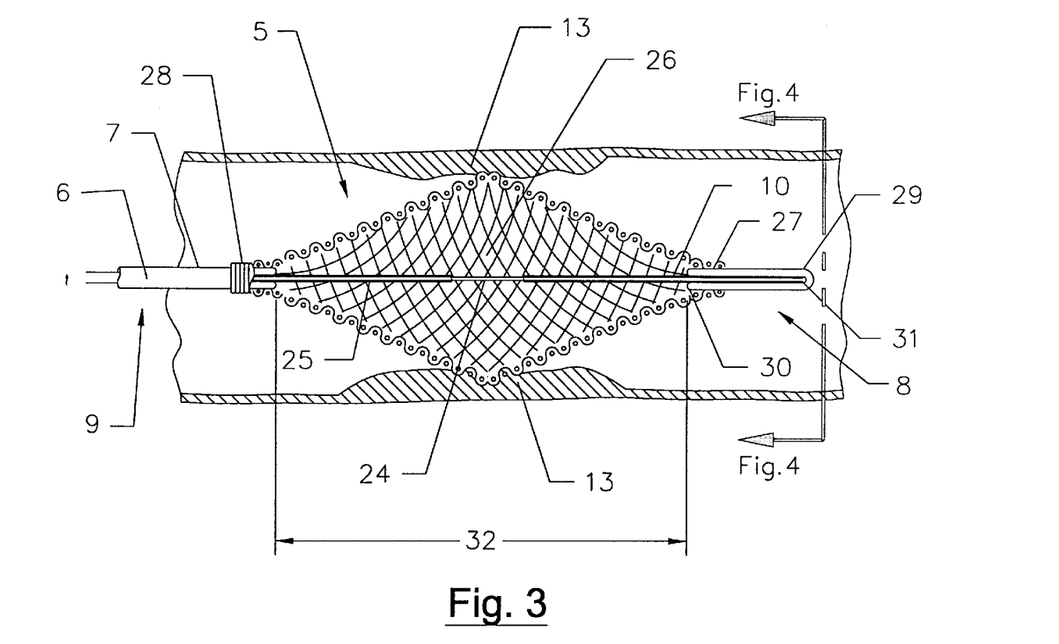
FIG. 3 is an enlarged longitudinal sectional view of the expandable braid device of FIG. 1 in a deployed configuration and positioned at the stenosis site.

Having described the general use of the expandable braid device 5 constructed according to this invention, the device 5 and the wire 6 to which the device 5 is attached are now further described. With reference to FIGS. 2 and 3, there is shown an enlarged view of the device 5 at the stenosis site 13 in collapsed (FIG. 2) and deployed (FIG. 3) configurations. In addition, FIG. 3 shows particular features of the wire 6 and the radiation source 24 attached to the inner core 25 of the device 5.

Figure 4:
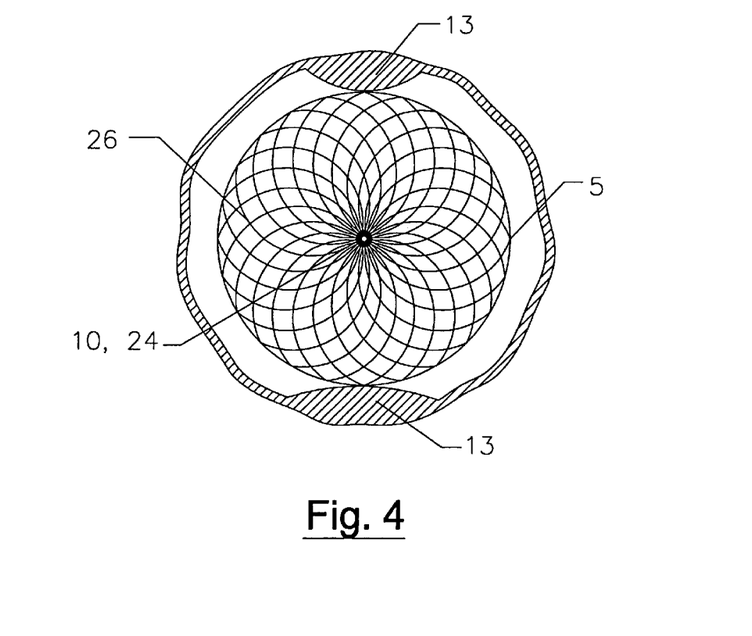
FIG. 4 is an enlarged cross-sectional view of the expandable braid device of FIG. 3, which is nearly fully deployed, taken along the line 4—4.

Referring to FIGS. 2 and 4, the expandable braid device 5 generally comprises the expandable braid 26 and the radiation device 24 located on or in the inner core 25. In an embodiment of the expandable braid 26, the braid 26 can comprise two or more relatively thin continuous wires having a cross section which is round, flat or otherwise suitable to form the braid 26. The braid 26 can be formed of high strength wires such as stainless steel, Co—Ni—Cr—Mo alloys, platinum or other suitable metal of high atomic number. Such materials can shield the radiation source 24 completely when the braid 26 is collapsed and partially when the braid 26 is partially deployed. In additional, in alternative embodiments, highly filled plastic may also provide shielding.

In an alternative embodiment of the expandable braid device 5, the braid 26 consists of fine mesh made of the same materials as described above for the interlacing wires. In this embodiment, it is contemplated that the size of the pores of mesh can be in the range of 40 to 500 microns, or other suitable size to provide exposure of the radiation source 24. In further alternative embodiments, the interlaced wire or fine mesh can consist of a thin composite metallic, or a plastic wire.

In an embodiment according to the present invention, the radiation source 24 can be any shaped radiation source, including, for example, a pellet, cylinder, wire or coil, attached to or a part of the inner core 25. The radiation source 24 is designed and adapted to deliver the intended dosage of radiation at the stenosis site 13. The dosage of the radiation source 24 to be delivered by the device 5, in terms of the total amount of radiation delivered to the site over the useful life of the device 5 and its rate, is selected according to the irradiation treatment plan. Accordingly, the dosage is determined based on the treatment plan and does not limit the present invention. In addition, the radiation source 24 can be composed of any type of radiation presently used for therapeutic purposes or hereinafter discovered since any radioactive composition for use in the irradiation procedure is contemplated as within the present invention. Examples of presently available Gamma radiation sources are cesium 137, cobalt 60, iodine 125, iodine 131, cobalt 57, iridium 192, gold 198, palladium 103, tantalum 73, tungsten 74, etc. Examples of presently available Beta radiation sources are phosphorus 32, strontium 90, and yttrium 90. In addition, treatment times could last between approximately four minutes to as long as thirty minutes or longer. Since iridium 192 has a well-defined energy level with a strength of one to two curies, it is particularly well suited to treat the area of the original stenosis at the prescribed distance. In this instance, treatment times would be in the range of five to ten minutes. Radioactive iridium 192 can also be impregnated into the inner core 25 of braid 26 for treatment times of between twenty to forty-five minutes. In addition, in alternative embodiments, the radiation source 24 can be titanium with phosphorous 32 placed within the braid 26, levels of 0.006 micro curies per cm of wire on which the source 24 is placed can be effective in humans in a range of 5.5 to 10.6 mm from the wire.

Referring to FIGS. 3 and 4, the expandable braid 26 is attached to a wire 6. The braid 26 can be designed to include a flexible distal end 27, such as, for example, a flexible spring member, and a flexible proximal end 28. The ends 27 and 28 are attached to the wire 6. The end 27 is bonded to the distal end portion 12 of the wire 6 to define a distal joint 30.

The distal end portion 12 of the wire 6 includes a distal end 29. The wire 6 also includes an outer sheath 7, which can be metal or plastic, having two sections. A distal section 8 is part of the distal end portion 12 and includes the flexible distal end 27 of the braid 26. A proximal section 9 includes the flexible proximal end 28 of the braid 26 and the portion of the wire 6 proximal to such end 28. The distal section 8 and the proximal section 9 are separated by an opening 32. The inner core 25 is located within a lumen 10 of the wire 6. The inner core 25 tapers radially inwardly to terminate in a shaped tip 31, which is attached to the distal end 29 of the wire 6. The radiation source 24 is located on the inner core 25 within the opening 32 such that when the expandable braid 26 is collapsed, the radiation source 24 is covered by such braid 26.

The mechanism which enables the expandable braid device 5 to operate and such operation are now described. The expandable braid 26 can then be deployed by actuating the control mechanism 15 to retract the inner core 25 longitudinally in the proximal direction. As the inner core 25 retracts, the tip 31 attached to the distal end 29 causes the distal end 27 similarly to move longitudinally in the proximal direction. As a result, the ends 27 and 28 of the braid 26 compress inwardly, thereby causing the length of the opening 32 to shorten and the braid 26 to expand radially outwardly against the stenosis site 13. In addition, the expandable braid 26 also can be deployed by manipulating the proximal end portion 14 of the wire 6 to advance the proximal section 9 of the sheath 7 longitudinally in the distal direction relative to the inner core 25 as well as the tip 31 remaining stationary. As a result, the ends 27 and 28 of the braid 26 are tensioned towards one another to cause the braid 26 to expand outward or buckle.

In addition, referring to FIGS. 3 and 4, deployment of the braid 26 outwardly along its radial axis causes the metallic filaments of the braid 26 to unwrap, thereby exposing the inner core 25 and the radiation source 24 contained on or within it to the stenosis site 13. The stenosis site 13 can then be treated with the radiation source 24 for a prescribed period of time for the irradiation treatment.

Furthermore, in an alternative embodiment, the expandable braid 26 can be partially deployed by partial movement of either the inner core 25 or the proximal section 9 of the sheath 7. Variations in the amount of deployment of the braid 26 provide attenuation of the radiation source 24 based on variations on the density of metallic material on the surface of the braid 26 in various stages of deployment. In this way, the physician can alter the amount of radiation provided to site, thereby providing variations in the radiation dosage without having to replace the braid 26 with another braid 26 having a different quantity or type for the radiation source 24.

Referring once again to FIGS. 3 and 4, in deployed configuration, the expandable braid 26 can be adapted to form a variety of shapes or configurations depending, for example, on the anatomy of the vessel 22 in which the braid will be inserted. For example, a diamond shape is shown for the expanded braid 26. In addition, a cylindrical or other appropriate shape can be designed should the particular shape of the vessel or design of irradiation therapy call for it. Such variations in shape are a design decision and, accordingly, any shape for the expandable braid 26 which accomplishes the function of shielding and exposing the radiation source 24 is contemplated as within the present invention.

Once the treatment concludes, the expandable braid 26 can be collapsed by actuating the control mechanism 15 to advance the inner core 25 longitudinally in the distal direction. As the inner core 25 advances, the stationary tip 31 causes the ends 27 and 28 of the braid 26 to tension outwardly, thereby causing the braid 26 to retract radially inwardly. In addition, the expandable braid 26 can be collapsed by manipulating the proximal end portion 14 of the wire 6 to retract the proximal section 9 longitudinally in the proximal direction relative to the inner core 25 as well as the tip 31 remaining stationary. As the proximal section 9 retracts along the inner core 25, the stationary tip 31 causes the ends 27 and 28 of the expandable braid 26 to tension away from one another, which, in turn, collapses the braid 26. When the braid 26 is collapsed, the radiation source 24 is once again shielded from exposure to the stenosis site 13 or any other portion of the vascular pathway 22.

In addition, the present invention contemplates a variety of mechanisms for deploying or collapsing the expandable braid 26. Such mechanisms are a design decision and, accordingly, any mechanism which accomplishes the function of expanding and closing the braid 26 to expose and shield the radiation source 24 is contemplated as within the present invention.

In alternative embodiments, the expandable braid 26 can be attached to a catheter or other delivery wire with a suitable mechanism to deploy and collapse the expandable braid 26. For example, each end 27 and 28 of the braid 26 can be connected to the surface of the catheter such that the braid 26 can be deployed and contracted by tensioning the points of connection of the expandable braid 26 to the catheter towards and away from each other, respectively.

In additional alternative embodiments of the present invention, the radioactive source 24 can be positioned on an expandable braid 26 protected shaft and delivered to the stenosis site 13 through a guide catheter. Also, the expandable braid device 5 can be miniaturized for delivery through the lumen of a balloon catheter. In this embodiment, the braid 26 can be introduced through the microcatheter and, after the distal end of the shaft containing the expandable braid 26 exits the distal end of the catheter, the braid 26 can be deployed. In addition, a wire exchange method can be used in which a tracking guide wire is removed from the lumen of a catheter and replaced with a wire 6 containing the expandable braid device 5. In another embodiment, the expandable braid device 5 can be tracking over a guide wire once the balloon catheter is removed.

Figures 5, 6:
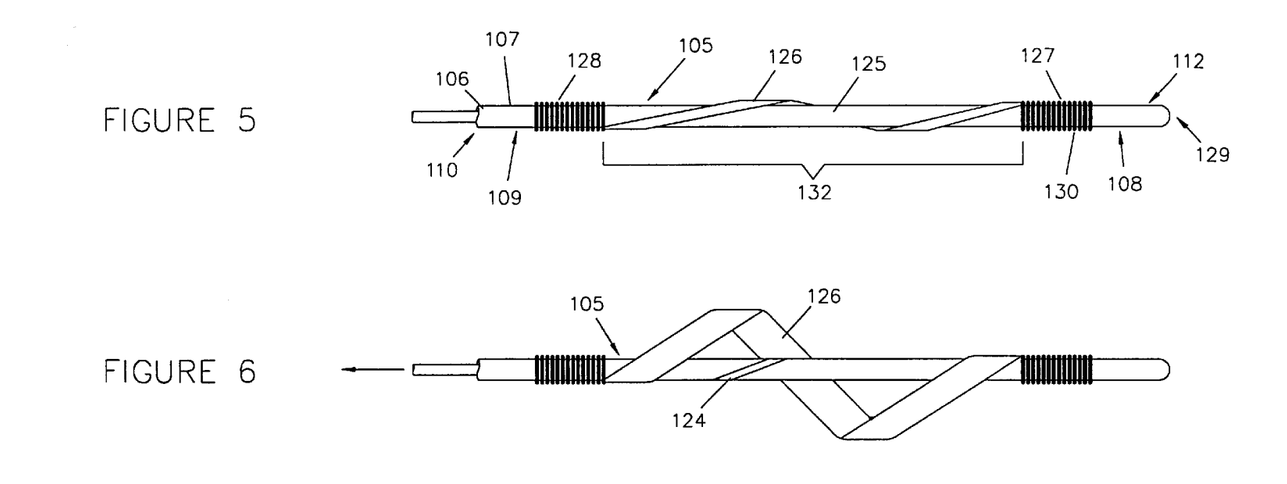
FIG. 5 is an enlarged longitudinal sectional view of an expandable spiral device constructed according to a first alternative embodiment of this invention, in a closed configuration and positioned at a stenosis site.
FIG. 6 is an enlarged longitudinal sectional view of the expandable spiral device of FIG. 5 in a partially deployed configuration and positioned at the stenosis site.
Figures 7, 8:
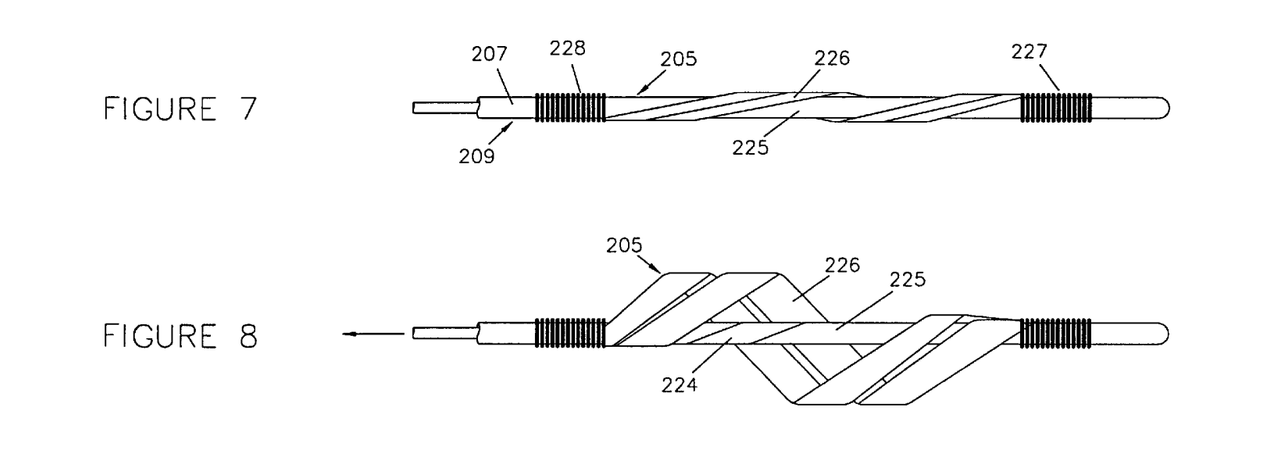
FIG. 7 is an enlarged longitudinal sectional view of the expandable spiral device constructed according to a second alternative embodiment of this invention, in a closed configuration and positioned at a stenosis site.
FIG. 8 is an enlarged longitudinal sectional view of the expandable spiral device of FIG. 7 in a partially deployed configuration and positioned at the stenosis site.

Referring to FIGS. 5 to 6, in further alternative embodiments, a metallic expandable coil or spiral device 105 or 205 can be used to perform the equivalent functions to the expandable braid device 5. These devices 105 and 205 can include an expandable spiral 126 or 226 comprising one or more relatively thin wires having a cross section which is round, flat or otherwise suitable to such spiral form. The configuration of the spiral 126 shown in FIGS. 5 and 6 includes one wire and a small number of windings. Where the spiral 226 includes two or more wires, the wires can interlace within the windings of each other in a follow the leader pattern, as shown in FIGS. 7 and 8. The spiral 126 contains multiple wires and a large number of windings. The expandable spirals 126 and 226 are equivalent to the braid 26 in the materials used for their construction (for example, metallic wire) and in the function of shielding and exposing radiation sources 124 and 224 to the stenosis sites 113 and 213 (not shown), respectively, on a number of different devices (for example, the wire 6), including any alternative embodiments described for the construction and function of the device 5 and the carrier on which such device 5 is implemented. Also, the radiation sources 124 and 224 are equivalent to such radiation source 24 usable for the device 5, including any alternative embodiments described for the radiation source 24.

Referring to FIG. 5, the configuration of the spiral 126 is a single metallic wire including a small number of windings. The spiral 126 is shown collapsed such that the windings act as an additional surface over the inner core 125. Referring to FIG. 6, the spiral 126 is shown in a deployed configuration. The radiation source 124 is shown in a spiral configuration with one winding such that it is oriented underneath the spiral 126. In this way, when the spiral 126 is collapsed (FIG. 5), it covers or shields the radiation source 124 and when the spiral 126 is deployed (FIG. 6), it exposes the radiation source to the stenosis site 113 (not shown).

Referring once again to FIGS. 5 and 6, the expandable spiral device 105 is equivalent to the expandable braid device 5 in its method of operation, including any alternative embodiments described for such device 5. Namely, the mechanism which enables the expandable spiral device 105 to operate and such operation are now described. The expandable spiral 126 is attached to a wire 106. The spiral 126 can be designed to include a flexible distal end 127, such as a flexible spring member, and a flexible proximal end 128. The ends 127 and 128 are attached to the wire 106. The end 127 is bonded to a distal end portion 112 of the wire 106 to define a distal joint 130.

The wire 106 includes the distal end portion 112 and a proximal end portion 114 (not shown) and a lumen 110. The distal end portion 112 includes a distal end 129. The wire 106 also includes an outer sheath 107 which has two sections. A distal section 108 is part of the distal end portion 112 of the wire 106 and includes the flexible distal end 127 of the spiral 126. A proximal section 109 includes the flexible proximal end 128 of the spiral 126 and the portion of the wire 106 proximal to such end 128. The distal section 108 and the proximal section 109 are separated by an opening 132. An inner core 125 is located within the lumen 110 of the wire 106. The inner core 125 tapers radially inwardly to terminate in a shaped tip 131 (not shown), which is attached to the distal end 129 of the wire 106. The radiation source 124 is located on the inner core 125 within the opening 132 such that when the expandable spiral 126 is collapsed, the radiation source 124 is covered by such spiral 126.

The expandable spiral 126 can be deployed by actuating the control mechanism 115 (not shown) to retract the inner core 125 longitudinally in the proximal direction. As the inner core 125 retracts, the tip 131 attached to the distal end 129 causes the distal end 127 similarly to move longitudinally in the proximal direction. As a result, the ends 127 and 128 of the spiral 126 compress inwardly, thereby causing the length of the opening 132 to shorten and the spiral 126 to expand radially outwardly against the stenosis site 113. In addition, the expandable spiral 126 also can be deployed by manipulating the proximal end portion 114 of the wire 106 to advance the proximal section 109 of the sheath 107 longitudinally in the distal direction relative to the inner core 125 as well as the tip 131 remaining stationary. As a result, the ends 127 and 128 of the spiral 126 are tensioned towards one another to cause the spiral 126 to expand or buckle.

In addition, referring to FIGS. 3 and 4, deployment of the spiral 126 outwardly along its radial axis causes the metallic filaments of the spiral 126 to unwrap, thereby exposing the inner core 125 and the radiation source 124 contained on or within it to the stenosis site 113. The stenosis site 113 can then be treated with the radiation source 124 for a prescribed period of time for the irradiation treatment.

Furthermore, in an alternative embodiment, the expandable spiral device 105 can be partially deployed in the same manner as the expandable braid device 5, including any alternative embodiments for such device 5.

Referring to FIGS. 7 and 8, the expandable spiral device 205 includes the same components as the expandable spiral device 105. In FIG. 7, the spiral 226 is shown collapsed such that the windings act as an additional surface over an inner core 225. In FIG. 8, the spiral 226 is shown in a deployed condition. The radiation source 224 is shown in a cylindrical configuration such that it is oriented underneath the spiral 226. In this way, when the spiral 226 is collapsed (FIG. 7), it covers or shields the radiation source 224 and when the spiral 226 is deployed (FIG. 8), it exposes the radiation source to the stenosis site 213 not shown). Like the embodiment illustrated in FIGS. 5 and 6, the present invention is not limited to a particular shape or configuration for the radiation source 224. Accordingly, the cylindrical shape of the source 224 is merely exemplary.

In this illustrative embodiment, the components used to operate the expandable spiral device 205 are the same as those for such device 105. Movement of either the inner core 225 or a proximal section 209 of a sheath 207 tensions a flexible distal end 227 and a flexible proximal end 228 towards or away from each other. In addition, However, the operation to deploy the spiral 226 can be the same as the operation to deploy the spiral 126 of FIGS. 5 and 6.

In addition, in alternative embodiments (not shown), the operation to deploy the spiral 226 can be the opposite of that to deploy the spiral 226 of FIGS. 7 and 8. That is, the ends 227 and 228 can be tensioned away from each other in order to stretch the spiral 226 and thereby cause gaps in between the windings of such spiral 226. The radiation source 224 is then exposed through such gaps. In addition, in order to collapse the spiral 226, the ends 227 and 228 are tensioned towards each other such that the windings of the spiral 226 are compressed. The spiral 226 thereby covers or shields the radiation source 224. Accordingly, the length of an opening 232 between ends 227 and 228 increases when the spiral 226 is deployed. In alternative embodiments, the spiral 226 may also be deployed and compressed based on a rotation motion.

For the embodiments shown in FIGS. 5 to 8, the variation in materials and configurations of and mechanisms to operate the expandable braid device 5, including the materials and configurations of the radiation source 24, also apply to such devices 105 and 205. Like the device 5, the devices 105 and 205 are not limited to the mechanisms of operation illustrated in FIGS. 5 to 8. Rather, the present invention contemplates any mechanism to operate the devices 5, 105 and 205 in order to fully or partially collapse and deploy the braid 26 and the spirals 126 and 226. In addition, numerous variations of the spirals 126 and 226 regarding the number of windings and the number of metallic wires for such spirals 126 and 226 are within the scope of the present invention. For example, the spiral 226 can be formed from one wire with multiple windings or greater than the two wires.

Figure 9:
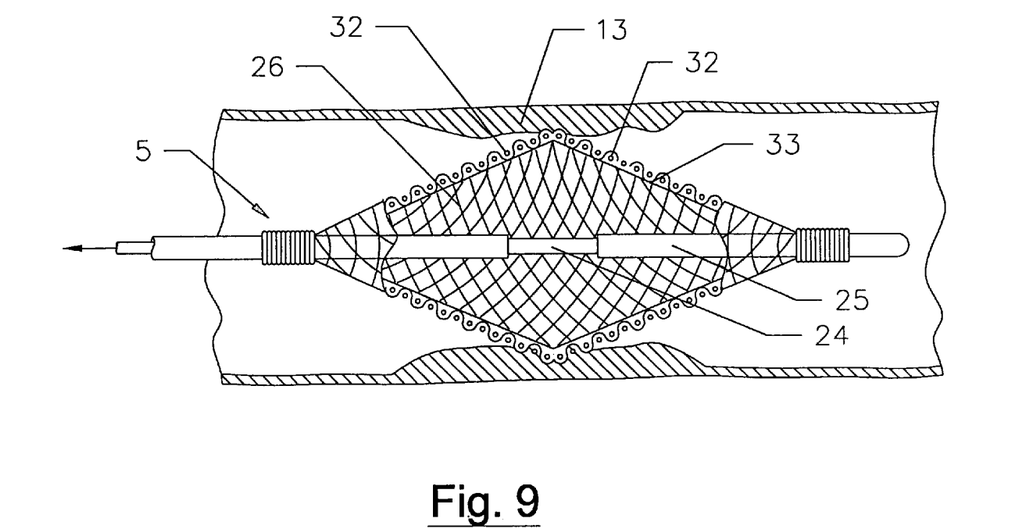
FIG. 9 is an enlarged longitudinal sectional view of the expandable braid device of FIG. 1 in a deployed configuration, positioned at the stenosis site and including radiation sources on an inner core of the device of FIG. 1 and on the inner surface of the braid of FIG. 1 according to a third alternative embodiment of the present invention.

Referring to FIG. 9, there is shown an enlarged longitudinal sectional view of the expandable braid device 5 of FIG. 1 in a deployed configuration, positioned at the stenosis site 13 and including the radiation source 24 on the inner core 25. In addition, another radiation source 32 is located on an inner surface 33 of the braid 26. In this figure, the radiation source 32 is a layer which can be applied to the inner surface of the braid 26. In alternative embodiments, the radiation source 32 can be pellets (shown in FIG. 10), an additional expandable braid, expandable spiral or any suitable configuration which can be secured to the inner surface 33 or located in the interior of the braid 26 such that when the braid 26 is collapsed, the radiation source 32 is shielded.

Such radiation source 32 provides a secondary source of radiation which can be different from the radiation source 24. For example, Beta radiation can be used for the radiation source 32 on the inner surface 33 while Gamma radiation can be used for the radiation source 24 within or on the inner core 25. Gamma radiation generally is particularly useful for exposure at a range or any distance from the stenosis site 13 while Beta radiation, which generally is particularly sensitive to distance (subject to a rapid decay from the source), is useful for exposure adjacent to the stenosis site 13. As a result, the embodiment of FIG. 9 optimizes such uses of the Gamma and Beta radiation. Further, the use of both radiation types optimizes the amount of radiation delivered to the stenosis site 13. In addition, the use and quantities of radiation types can be varied depending on the irradiation treatment plan. An example of such dual radiation sources 24 and 32 are as follows: the inner core 25 of the braid 26 is treated to contain $^{55}$Co, $^{56}$Co, $^{51}$Cr, $^{52}$Mn, $^{57}$Ni and $^{55}$Fe to emit Beta, Gamma and X-rays with half-lives between 17.5 hours ($^{55}$Co) and 2.7 years ($^{55}$Fe). Dual sources would be beneficial where a single source of radiation (e.g., low Gamma) has too low an intensity to be useful but is less risky for exposing the physician to radiation than a higher source. This single source can then be coupled with a second source of radiation (e.g., low Beta) to provide adequate radiation for the treatment.

Figure 10:
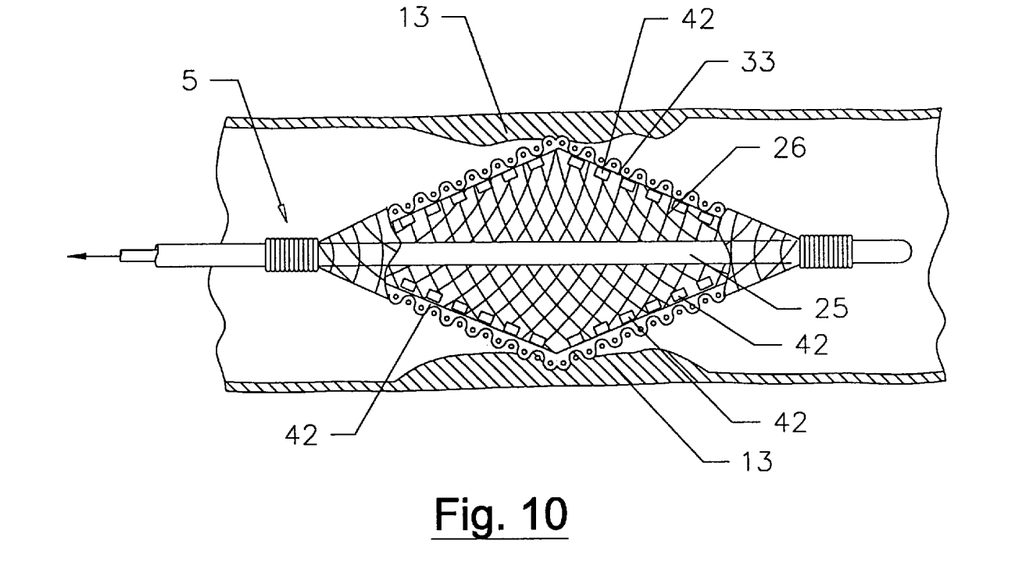
FIG. 10 is an enlarged longitudinal sectional view of the expandable braid device of FIG. 1 in a deployed configuration, positioned at the stenosis site and including a radiation source on the inner surface of the braid of FIG. 1 according to a fourth alternative embodiment of the present invention.

Referring to FIG. 10, there is shown an enlarged longitudinal sectional view of the expandable braid device 5 of FIG. 1 in a deployed configuration, positioned at the stenosis site 13 and including a radiation source 42 on the inner surface 33 of the braid 26. The radiation source 42 is configured as a number of disks which are attached to the inner surface 33 such that when the braid is collapsed, the source 42 is shielded. Accordingly, the radiation source 32 can be used alone (FIG. 10) or in combination with the radiation source 24 (FIG. 9) to provide a variety of treatments to the stenosis site 13. In addition, the use and function of additional radiation sources 32 and 42 apply to the expandable spiral devices 105 and 205 shown in FIGS. 5 to 8 as well.

Moreover, in further alternative embodiments, such additional radiation sources 32 and 42 can be located anywhere in the interior of such braid 26 or spirals 126 and 226, in addition to the inner surface 33, such that they provide a separate or second radiation source to the stenosis site 13.

Having thus described the present invention, it is to be understood that the above-described device and method are illustrative of the principals of this invention and that other embodiments may be devised by those skilled in the art, without departing from the spirit and scope of the invention. Accordingly, the invention is not limited by the specific examples illustrated herein, but by the appended claims.

What is claimed is:

1. An irradiation device for providing radiation treatment to a lesion in an artery, comprising:

a flexible elongated member insertable into said artery;

an expandable structure secured to said member and deliverable to said lesion by advancing said member in said artery; and a radiation source located within said expandable structure;

said expandable structure being collapsed during delivery to said lesion, whereby said radiation source is shielded from said artery and being expanded near said lesion to expose said radiation source to said lesion.

2. The device of claim 1 further comprising:

said elongated member being a hollow tube and including at least a first and second section with an opening between them; and a flexible wire within said member, said radiation source being secured to said wire and located within said opening.

3. The device of claim 2 and further including means for fully or partially expanding said expandable structure near said lesion.

4. The device of claim 2 wherein said expandable structure is one of a braid, a mesh structure and a spiral coil, said spiral coil including at least one wire.

5. The device of claim 2 wherein said radiation source is located at a radial core of said expandable structure.

6. The device of claim 1 wherein said expandable structure is one of a braid, a mesh structure and a spiral coil, said spiral coil including at least one wire.

7. The device of claim 6, wherein said spiral coil includes at least two wires.

8. An irradiation device for providing radiation treatment to a lesion in an artery, comprising:

a flexible elongated member insertable into said artery;

an expandable structure secured to said member and deliverable to said lesion by advancing said member in said artery;

a radiation source located within said expandable structure;

said expandable structure being collapsed during delivery to said lesion, whereby said radiation source is shielded from said artery; and being one of fully or partially deployed near said lesion to expose said radiation source to said lesion.

9. An irradiation device for providing radiation treatment to a lesion in an artery, comprising:

a flexible elongated member insertable into said artery and having a distal portion;

an expandable structure secured to said distal portion and deliverable to said lesion by advancing said member in said artery;

a radiation source located within said expandable structure;

said expandable structure being collapsed during delivery to said lesion, whereby said radiation source is shielded from said artery; and means for contracting said expandable structure to expand said expandable structure and thereby to expose said radiation source to said lesion.

10. The device of claim 9 wherein:

said elongated member is a hollow tube and including at least a first and second section with an opening between them, said device further comprising a flexible wire within said member, said radiation source being secured to said wire and located within said opening.

11. The device of claim 10 wherein said expandable structure is one of a braid, a mesh structure and a spiral coil, said spiral coil including at least one wire.

12. The device of claim 10 wherein said radiation source is located at the radial core of said expandable structure.

13. The device of claim 9 wherein said contracting means comprises means for fully or partially expanding said expandable structure.

14. The device of claim 9 wherein said expandable structure is one of a braid, a mesh structure and a spiral coil, said spiral coil including at least one wire.

15. The device of claim 14 wherein said spiral coil includes at least two wires.

16. A method for providing radiation treatment to a lesion in an artery, said method comprising the steps of:

inserting into said artery a flexible elongated member having a radiation source secured thereto, said radiation source being shielded from exposure to said artery by a collapsed expandable structure; and causing said expandable structure to expand within said artery to expose said lesion to said radiation source.

17. The method in accordance with claim 16 wherein said step of expanding said expandable structure includes controlling the amount of expansion to attenuate the amount of exposure of said lesion to said radiation source.

18. An irradiation device for providing radiation treatment to a lesion in an artery, comprising:

a flexible elongated member insertable into said artery;

an expandable structure secured to said member and deliverable to said lesion by advancing said member in said artery;

a plurality of radiation sources, a first radiation source located at a radial core of said expandable structure and a second radiation source located in an interior of said expandable structure;

said expandable structure being collapsed during delivery to said lesion, whereby said plurality of radiation sources are shielded from said artery; and said expandable structure being expanded near said lesion to expose said plurality of radiation sources to said lesion.

19. The device of claim 18 wherein said first radiation source is a Gamma source and said second radiation source is a Beta source.

20. The device of claim 18 wherein said second radiation source is located in the interior of said expandable structure other than said radial core.

21. An irradiation device for providing radiation treatment to a lesion in an artery, comprising:

a flexible elongated member insertable into said artery;

a collapsed expandable structure secured to said member and deliverable to said lesion by advancing said member in said artery;

a plurality of radiation sources, a first radiation source located at a radial core of said expandable structure and a second radiation source located in an interior of said expandable structure, said plurality of radiation sources being shielded form said artery during delivery to said lesion by said collapsed expandable structure; and means for contracting said expandable structure to expand said expandable structure and thereby to expose said plurality of radiation sources to said lesion.

22. The device of claim 21 wherein said first radiation source is a Gamma source and said second radiation source is a Beta source.

23. The device of claim 21 wherein said second radiation source is located in the interior of said expandable structure other than said radial core.

24. A method for providing radiation treatment to a lesion in an artery, said method comprising the steps of:

inserting into said artery a flexible elongated member having a plurality of radiation sources secured thereto, said plurality of radiation sources being shielded from exposure to said artery by a collapsed expandable structure, a first radiation source located at a radial core of said expandable structure and a second radiation source located in an interior of said expandable structure; and causing said expandable structure to expand within said artery to expose said lesion to said plurality of radiation sources.

25. The method of claim 24 wherein said first radiation source is a Gamma source and said second radiation source is a Beta source.

26. The method of claim 24 wherein said second radiation source is located in the interior of said expandable structure other than said radial core.

27. The method in accordance with claim 24 wherein said step of expanding said expandable structure includes controlling the amount of expansion to attenuate the amount of exposure of said lesion to said radiation sources.

28. A method for controlling the amount of radiation to a lesion in an artery, said method comprising the steps of:

inserting into said artery a flexible elongated member having a radiation source secured thereto, said radiation source being shielded from exposure to said artery by a collapsed expandable structure; and controlling the amount of expansion of said expandable structure.

* * * * *